United States Patent [19]

Sprecker

[11] 4,349,449
[45] Sep. 14, 1982

[54] PROCESS FOR ENHANCING OR AUGMENTING THE AROMA OF DETERGENTS USING NORBORNYL ESTERS

[75] Inventor: Mark A. Sprecker, Sea Bright, N.J.

[73] Assignee: International Flavors & Fragrances Inc., New York, N.Y.

[21] Appl. No.: 310,909

[22] Filed: Oct. 13, 1981

Related U.S. Application Data

[60] Division of Ser. No. 247,321, Mar. 25, 1981, Pat. No. 4,315,945, which is a continuation-in-part of Ser. No. 200,012, Oct. 23, 1980, Pat. No. 4,311,861.

[51] Int. Cl.$^3$ .................................................. C11D 3/50
[52] U.S. Cl. .............................. 252/174.11; 252/8.6; 252/132; 252/DIG. 13
[58] Field of Search .............. 252/174.11, 522 R, 132; 260/348.51; 568/665, 666

[56] References Cited

U.S. PATENT DOCUMENTS 3,927,116 12/1975 Rick et al. ............................ 568/665
4,218,347 8/1980 Näf et al. ............................ 252/522 R
4,246,129 1/1981 Kacher .................................. 252/90
4,310,681 1/1982 Klemarczyk et al. .............. 560/120

*Primary Examiner*—P. E. Willis, Jr.
*Attorney, Agent, or Firm*—Arthur L. Liberman

[57] ABSTRACT

Described are processes and compositions for augmenting or enhancing the flavor and/or aroma of consumable materials including foodstuffs, chewing gums, medicinal products, toothpastes, perfumes, colognes and perfumed articles using as the essential ingredient at least one norbornyl ether having the structure:

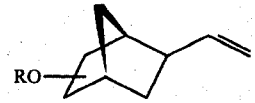

wherein R is one of acetyl, propionyl, allyl or isopropyl.

1 Claim, No Drawings

PROCESS FOR ENHANCING OR AUGMENTING THE AROMA OF DETERGENTS USING NORBORNYL ESTERS

This is a divisional of application Ser. No. 247,321, filed Mar. 25, 1981, now U.S. Pat. No. 4,315,945 which in turn, is a continuation-in-part of U.S. Letters Pat. Ser. No. 200,012 filed on Oct. 23, 1980, now U.S. Pat. No. 4,311,861.

BACKGROUND OF THE INVENTION

The instant invention provides novel norbornyl ethers having the structure:

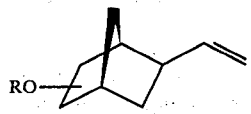

wherein R is one of acetyl, propionyl, allyl or isopropyl.

Materials which can provide green, anisic, floral, fruity, spicy aromas with costus-like and coffee/mocha-like undertones are known in the art of perfumery. Many of the natural materials which provide such fragrances and contribute the desired nuances to perfumery compositions are high in cost, vary in quality from one batch to another and/or are generally subject to the usual variations of natural products.

By the same token, materials which can provide sweet, anise-like, fennel, licorice-like, hay, green, herbaceous, spicy and floral aroma and taste profiles with bitter tastes are well known in the art of flavoring for foodstuffs, toothpastes, chewing gums and medicinal products. Many of the natural materials which provide such flavor notes and contribute desired nuances to flavor and compositions are high in cost, vary in quality from one batch to another and/or are generally subject to the usual variations of natural products.

There is, accordingly, a continuing effort to find synthetic materials which will replace, enhance or augment the essential flavor and fragrance notes provided by natural essential oils or compositions thereof. Unfortunately, many of these synthetic materials either have the desired nuances only to a relatively small degree or else contribute undesirable or unwanted odor to the compositions. The search for materials which can provide more refined licorice-like flavor, for example, has been difficult and relatively costly in the areas of both natural products and synthetic products.

Artificial flavoring agents for foodstuffs have received increasing attention in recent years. For many years, such food flavoring agents have been preferred over natural flavoring agents at least in part due to their diminished cost and their reproducible flavor qualities. For example, natural food flavoring agents such as extracts, concentrates and the like are often subject to wide variations due to changes in quality, type and treatment of the raw materials. Such variations can be reflected in the end products and result in unfavorable flavor characteristics in said end products. Additionally, the presence of the natural product in the ultimate food may be undesirable because of increased tendency to spoil. This is particularly troublesome in food and food uses where such products as dips, soups, chips, sausages, gravies and the like are apt to be stored prior to use.

The fundamental problem in creating artificial flavor agents is that the artificial flavor to be achieved be as natural as possible. This generally proves to be a difficult task since the mechanism for flavor development in many foods, medicinal products, chewing gums and toothpastes is not completely known. This is noticeable in products having licorice, anise-like, root beer-like and fennel-like taste characteristics particularly.

Even more desirable are products that can serve to substitute for difficult-to-obtain natural perfumery oils and, at the same time, substitute for natural flavoring ingredients in foodstuffs, chewing gums, medicinal products and toothpastes.

The parent application of the instant case, U.S. application for Letters Patent Ser. No. 200,012 filed on Oct. 23, 1980, now U.S. Pat. No. 4,311,861, describes compounds having the structures:

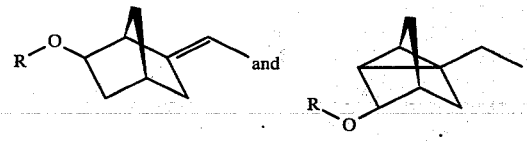

wherein R represents $C_3$-$C_6$ alkyl; aralkyl; hydroxy alkyl; and alkoxy alkyl, and uses thereof in augmenting or enhancing the aroma of perfume compositions, colognes, and perfumed articles (including fabric softener compositions, fabric softener articles, hair conditioners, floor waxes, solid or liquid anionic, cationic, nonionic or zwitterionic detergents, and deodorant compositions and deodorant articles), as well as processes for preparing such compounds.

The compounds defined according to the structure:

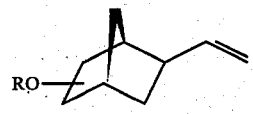

wherein R is one of acetyl, propionyl, allyl or isopropyl, have not been disclosed to be useful for their organoleptic properties, however, such compounds are known in the art. Thus, U.S. Pat. No. 3,927,116 discloses compounds having the structure:

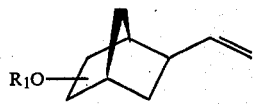

wherein $R_1$ represents hydrogen or $C_1$-$C_{20}$ acyl or alkyl.

Nothing in said U.S. Pat. No. 3,927,116 or any other prior art discloses the organoleptic utilities of the compounds of our invention defined according to the structure:

wherein R is one of acetyl, propionyl, allyl or isopropyl.

THE INVENTION

It has now been determined that certain norbornyl ethers and esters are capable of imparting a variety of flavors and fragrances to various consumable materials and are also capable of augmenting or enhancing a variety of flavors and fragrances of various consumable materials. Briefly, our invention contemplates augmenting or enhancing the flavors and/or fragrances of such consumable materials as perfumes, perfumed articles, colognes, foodstuffs, chewing gums, toothpastes and medicinal products by adding thereto a small, but effective, amount of at least one norbornyl ether or ester having the structure:

wherein R is one of acetyl, propionyl, allyl or isopropyl.

The norbornyl ethers and esters of our invention augment or enhance the green, anisic, floral, fruity and spicy aromas of perfume compositions, perfumed articles and colognes. The norbornyl ethers and esters of our invention also augment or enhance the sweet, anise-like, fennel, licorice-like, hay, green, herbaceous, spicy and floral aroma and taste of foodstuffs, toothpastes, medicinal products and chewing gums.

Examples of the norbornyl ethers and esters of our invention and their organoleptic characteristics are as follows:

TABLE I

| Structure of the Compound | Flavor Characteristics | Fragrance Characteristics |
|---|---|---|
| (acetyl) | A sweet, anise, fennel aroma and taste profile at 0.2 ppm making it useful in root beer, licorice and anise flavored foodstuffs. | A green, anisic and floral aroma with costus-like undertones. |
| (propionyl) | A sweet, anise, licorice, fennel, hay, green aroma and taste profile at 1 ppm making it useful in anise, fennel and licorice flavors. | A floral, anisic, fruity, chamomile/basil-like aroma profile. |
| (allyl) | A sweet, anise, licorice, green, herbaceous and spicy aroma and taste profile with bitter taste nuances. | A spicy, fruity aroma with coffee-mocha undertones. |
| (isopropyl) | A sweet, green, floral and herbaceous aroma and taste with bitter taste nuances at 5 ppm. | |

TABLE I-continued

| Structure of the Compound | Flavor Characteristics | Fragrance Characteristics |
|---|---|---|
| (HO-) | A balsamic aroma and taste. | A fruity aroma. |

The norbornyl ethers and esters of our invention can be prepared according to the process as set forth in United States Letters Pat. No. 3,927,116.

When the norbornyl ethers and esters of our invention are used as food flavor adjuvants, the nature of the co-ingredients included with said norbornyl ethers and esters in formulating the product composition will also serve to alter, modify, augment or enhance the organoleptic characteristics of the ultimate foodstuff treated therewith.

As used herein in regard to flavors, the term "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste."

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

As used herein, the term "medicinal product" includes both solids and liquids which are ingestible, non-toxic materials which have medicinal value such as cough syrups, cough drops, aspirin and chewable medicinal tablets.

The term "chewing gum" is intended to mean a composition which comprises a substantially water insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine, and a flavoring composition which incorporates one or more of the norbornyl ethers and esters of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material by "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising, broadly, stabilizers, thickeners, surface active agents, conditioners, other flavorants and flavor intensifiers.

Stabilizer compounds include preservatives, e.g., sodium chloride; antioxidants, e.g., clacium and sodium ascorbate, ascorbic acid, butylated hydroxyanisole (mixture of 2- and 3-tertiary-butyl-4-hydroxy-anisole), butylated hydroxytoluene (2,6-di-tertiary-butyl-4-methyl phenol), propyl gallate and the like, and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids, carbohydrates, starches, pectins and emulsifiers, e.g., mono-and diglycerides of fatty acids, skim milk powder, hexoses, pentoses, di-saccharides, e.g., sucrose, corn syrup and the like.

Surface active agents include emulsifying agents, e.g. fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, butters and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum clacium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methylbutyric acid, propionic acid, valeric acid, 2-methyl-2-pentenoic acid, and 2-methyl-3-pentenoic acid; ketones and aldehydes, e.g., acetaldehyde, acetophenone, actone, acetyl methyl carbinol, acrolein, n-butanal, crotonal, diacetyl, 2-methylbutanal, beta,beta-dimethylacrolein, methyl n-amyl ketone, n-hexanal, 2-hexenal, isopentanal, hydrocinnamic aldehyde, cis-3-hexenal, 2-heptenal, nonyl aldehyde, 4-(p-hydroxyphenyl)-2-butanone, alpha-ionone, beta-ionone, 2-methyl-3-butanone, benzaldehyde, damascone, α-damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl-furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, ph-hydroxyphenyl-2-ethanol, isoamyl alcohol, isofenchyl alcohol, phenyl-2-ethanol, alpha-terpineol, cis-terpin hydrate, eugenol, linalool,2-heptanol, acetoin; ester, such as butyl acetate, ethyl acetate, ethyl acetoacetate, ethyl benzoate, ethyl butyrate, ethyl caprate, ethyl caproate, ethylcarpylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate,hexyl acetate, 2-hexenyl butyrate, hexyl butyrate, isoamyl acetate, isopropyl butyrate, methyl acetate, methyl butyrate, methyl caproate, methyl isobutyrate, alpha-methyl-phenylglycidate, ethyl succinate, isobutyl cinnamate, cinnamyl formate, methyl cinnamate and terpenyl acetate; hydrocarbons such as dimethyl naphthaline, dodecane, methyldiphenyl, methyl naphthalene, myrcene, naphthalene, octadecane, tetradecane, tetramethyl-naphthalene, tridecane, trimethylnaphthalene, undecane, caryophyllene, α-phellandrene, β-phellandrene, p-cymene-1-alpha-pinene, beta-pinene, dihydrocarveol; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils such as jasmine absolute, cassia oil, cinnamon bark oil, black pepper oleo-resin, oil of black pepper, rose absolute, orris absolute, oil of cubeb, oil of coriander, oil of pimento leaf, oil of patchouli, oil of nutmeg, lemon essential oil, safran oil, Bulgarian rose, capsicum, yara yara and vanilla; lactones such as γ-nonalactone; sulfides, e.g., methyl sulfide and other materials such as maltol and acetals (e.g., 1,1-diethoxyethane, 1,1-dimethoxyethane and dimethoxymethane), piperine, chavicine and piperidine.

The specific flavoring adjuvant selected for use may be either solid or liquid depending upon the desired physical form of the ultimate product, i.e., foodstuff, whether simulated or natural, and should, in any event, (i) be organoleptically compatible with the norbornyl ethers and esters of our invention by not covering or spoiling the organoleptic properties (aroma and/or taste) thereof; (ii) be non-reactive with the norbornyl ethers and esters of our invention and (iii) be capable of providing an environment in which the norbornyl ethers and esters can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of norbornyl ethers and esters of our invention employed in a particular instance can vary over a relatively wide range, depending upon the desired organoleptic effects to be achieved. Thus, correspondingly, greater amounts would be necessary in those instances wherein the ultimate food composition to be flavored (e.g., with a spice flavor or a specific black pepper-like flavor) is relatively bland to the taste, whereas relatively minor quantities may suffice for purposes of enhancing the composition merely deficient in natural flavor or aroma. The primary requirement is that the amount selected be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of norbornyl ethers or esters will, of course, substantially vitiate any possibility of obtaining the desired results while excess quantities prove needlessly costly and in extreme cases may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of norbornyl ethers and esters ranging from a small but effective amount, e.g., 0.5 ppm up to about 100 ppm based on total composition, are suitable. Concentrations in excess of the maximum quantity stated are not normally recommended since they fail to provide commensurate enhancement of organoleptic properties. In those instances wherein the norbornyl ethers and esters are added to the foodstuff as an integral component of a flavoring composition, it is of course essential that the total quantity of flavoring composition employed be sufficient to yield an effective norbornyl ether and ester concentration in the foodstuff product.

Food flavoring compositions prepared in accordance with the present invention preferably contain the norbornyl ethers and esters in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the norbornyl ethers and esters with, for example, gum arabic, gum tragacanth, carrageenan and the like, and thereafter spray-drying the resultant mixture whereby to obtain the particular solid product. Preprepared flavor mixes in powder form, e.g., a fruit-flavored powder mix, are obtained by mixing the dried solid components, e.g., starch, sugar and the like, and norbornyl ethers and esters in a dry blender until the requisite degree of uniformity is achieved.

It is presently preferred to combine with the norbornyl ethers and esters of our invention, the following adjuvants:
Oil of cubeb;
phellandrene;
β-phellandrene;
Oil of coriander;
Oil of pimento leaf;
Oil of patchouli;
Alpha Pinene;
Beta Pinene;
Beat-caryophyllene;
Dihydrocarveol;
piperonal;
Piperine;
Chavicine;
Piperidine;
Oil of black pepper;
Black pepper oleoresin;
Capsicum;
Oil of nutmeg;
Cardamom oil
Clove oil;
Spearmint oil; and
Oil of peppermint.

The norbornyl ethers and esters of our invention can be used to contribute green, anisic, floral, fruity and spicy aromas with costus-like and coffee/mocha-like undertones to perfume compositions and perfumed articles. As olfactory agents, the norbornyl ethers and esters of our invention can be formulated into or used as components of a perfume composition.

The term "perfume composition" is used herein to mean a mixture of organic compounds including, for example, alcohols, aldehydes, ketones, nitriles, ethers, and frequently hydrocarbons which are admixed so that the combined odors of the individual components produce a pleasant or desired fragrance. Such perfume compositions usually contain: (a) the main note of the "bouquet" or foundation-stone of the composition; (b) modifiers which round-off and accompany the main note; (c) fixatives which include odorous substances which lend a particular note to the perfume throughout all stages of evaporation, and substances which retard evaporation; and (d) top-notes which are usually low-boiling, fresh-smelling materials.

In perfume compositions the individual component will contribute its particular olfactory characteristics, but the overall effect of the perfume composition will be the sum of the effect of each ingredient. Thus, the individual compounds of this invention, or mixtures thereof, can be used to alter the aroma characteristics of a perfume composition, for example, by highlighting or moderating the olfactory reaction contributed by another ingredient in the composition.

The amount of the norbornyl ethers and esters of this invention which will be effective in perfume compositions depends on many factors, including the other ingredients, their amounts and the effects which are desired. It has been found that perfume compositions containing as little as 2% of the norbornyl ethers and esters of this invention, or even less, can be used to impart an interesting citrusy and/or spicy and/or anisic aroma to soaps, cosmetics and the other products. The amount employed can range up to 50% or higher and will depend on considerations of cost, nature of the end product, and the effect desired on the finished product and particular fragrance sought.

The norbornyl ethers and esters of this invention can be used alone or in a perfume composition as an olfactory component in detergents and soaps, space odorants and deodorants; perfumes; colognes, toilet waters; bath salts; hair preparations such as lacquers, brilliantines, pomades, and shampoos; cosmetic preparations such as creams, deodorants, hand lotions, and sun screens; powders such as talcs, dusting powders, face powder, and the like. When used as an olfactory component of a perfumed article, as little as 0.01% of one or more of the norbornyl ethers and esters will suffice to impart an interesting citrusy and/or spicy and/or anisic aroma. Generally no more than 0.5% is required.

In addition, the perfume composition can contain a vehicle or carrier for the norbornyl ethers or esters alone or with other ingredients. The vehicle can be a liquid such as an alcohol such as ethanol, a glycol wuch as propylene glycol, or the like. The carrier can be an absorbent solid such as a gum or components for encapsulating the composition.

The following examples are given to illustrate embodiments of the invention as it is presently preferred to practice it. It will be understood that these examples are illustrative, and the invention is not to be considered as restricted thereto except as indicated in the appended claims.

EXAMPLE I

Pine fragrance using a mixture of 5- and 6-vinyl-2-norbornanol acetate defined by the structure:

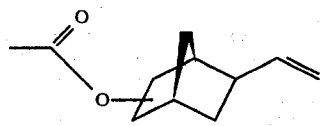

The following mixture is prepared:

| | |
|---|---|
| Isobornyl acetate | 20% |
| Beta Pinene | 10% |
| Cedryl acetate | 10% |
| Terpinyl acetate | 10% |
| Pine needle oil, Siberian | 4% |
| Linalyl acetate | 16% |
| Amyl cinnamic aldehyde | 10% |
| 50:50 mixture of 5- and 6-vinyl-2-norbornanol acetate | 20% |

The mixture of 5- and 6-vinyl-2-norbornanol acetate imparts a green, anisis, floral aroma and costus undertone which is quite powerful to this pine fragrance.

EXAMPLE II

HERBAL FRAGRANCE

The following mixture is prepared:

| | |
|---|---|
| Amyl cinnamic aldehyde | 20% |
| Phenyl acetaldehyde dimethyl acetal | 4% |
| Thyme oil, white | 8% |
| Sauge sclaree French | 8% |
| Galbanum oil | 4% |
| Geranyl acetate | 10% |
| Juniper berry oil | 4% |
| Methyl octin carbonate | 2% |
| Linalyl acetate | 10% |
| Dihydro methyl jasmonate | 20% |
| Mixture (50:50) of 2-allyloxy-5- and 6-vinyl norbornane | 10% |

The mixture (50:50) of 2-allyloxy-5- and 6-vinyl norbornanes adds a strong floral, anisic aroma with a fruity and spicy character and chamomile/basil undertones.

EXAMPLE III

PRODUCTION OF A ROSEMARY FRAGRANCE

The following mixture is prepared:

| | |
|---|---|
| Borneol | 20% |
| French turpentine | 20% |
| Camphor gum | 20% |
| Thymol-10% in diethyl phthalate | 2% |
| Eucalyptol | 20% |
| Isobornyl acetate | 10% |
| Fenchone | 4% |
| 50:50 mixture of 5- and 6-vinyl-2-norbornane methanol propionate | 4% |

The 50:50 mixture of 5- and 6-vinyl-2-norbornane methanol propionate adds a spicy, fruity aroma with a coffee/mocha undertone to this rosemary fragrance.

EXAMPLE IV

PREPARATION OF SOAP COMPOSITIONS 100 grams of soap chips (IVORY ®, a trademark of the Procter & Gamble Company of Cincinnati, Ohio) are mixed with 1 gram of one of the perfumery substances set forth in Table II below until a substantially homogeneous composition is obtained. The mixture is then heated to 180° C. while being maintained under a pressure of 35 atmospheres until a homogeneous liquid is obtained. The liquid is maintained at 35 atmospheres pressure and 180° C. for three hours. The mixture is then quickly chilled to 0° C. and the resulting solid soap is cut up into cakes. Each of the perfumed soap cakes manifests excellent perfume compositions as set forth in Table II below:

TABLE II

| Substance | Fragrance Character |
|---|---|
| Compound having the structure: (structure shown) | A green, anisic and floral aroma with costus-like undertones. |
| Compound having the structure: (structure shown) | A floral, anisic, fruity, chamomile/basil-like aroma profile. |
| Compound having the structure: (structure shown) | A spicy, fruity aroma with coffee-mocha undertones. |
| Compound having the structure: (structure shown) | A fruity aroma. |
| Perfume composition prepared according to Example I. | A pine aroma with excellent green, anisic, floral nuances and costus-like undertones. |
| Perfume composition prepared according to Example II. | An herbal fragrance having floral and anisic aroma nuances with a fruity, spicy character and chamomile and basil undertones. |
| Perfume composition prepared according to Example III. | A rosemary fragrance with spicy and fruity aroma nuances and a coffee/mocha undertone. |

EXAMPLE V

PREPARATION OF A DETERGENT COMPOSITION

A granular detergent composition is prepared according to Example 9 of Canadian Pat. No. 1,004,566 containing the following ingredients:

| Component | Weight % |
|---|---|
| Anhydrous sodium carbonate | 30.0 |
| Hydrated sodium silicate (81.5% solids, SiO$_2$—Na$_2$O ratio- 2.1:1 by weight | 20.0 |
| Coconut alcohol condensed with 6 molar proportions of ethylene oxide | 10.0 |
| Sodium citrate dihydrate | 10.0 |
| Sodium dichlorocyanurate dihydrate | 3.8 |
| Polyethylene glycol (available under the trademark Carbowax ® 4000; M.W. 3000–3700) | 2.0 |
| Dimethyl silicone | 0.8 |
| Anhydrous sodium sulfate | 15.5 |
| Substance as set forth in Table III | 5.9 |

This composition has an excellent aroma as set forth in Table III below:

TABLE III

| Substance | Fragrance Character |
|---|---|
| Compound having the structure: | A green, anisic and floral aroma with costus-like undertones. |
| Compound having the structure: | A floral, anisic, fruity, chamomile/basil-like aroma profile. |
| Compound having the structure: | A spicy, fruity aroma with coffee-mocha undertones. |
| Compound having the structure: | A fruity aroma. |
| Perfume composition prepared according to Example I. | A pine aroma with excellent green, anisic, floral nuances and costus-like undertones. |
| Perfume composition prepared according to Example II. | An herbal fragrance having floral and anisic aroma nuances with a fruity, spicy character and chamomile and basil undertones. |
| Perfume composition prepared according to Example III. | A rosemary fragrance with spicy and fruity aroma nuances and a coffee/mocha undertone. |

EXAMPLE VI

PREPARATION OF A COSMETIC POWDER COMPOSITION

Cosmetic powders are prepared by mixing in a ball mill 100 grams of talcum powder with 0.25 grams of the substance as set forth in Table IV below. Each of the cosmetic powders has excellent aromas as set forth in Table IV below:

TABLE IV

| Substance | Fragrance Character |
|---|---|
| Compound having the structure: | A green, anisic and floral aroma with costus-like undertones. |
| Compound having the structure: | A floral, anisic, fruity, chamomile/basil-like aroma profile. |
| Compound having the structure: | A spicy, fruity aroma with coffee-mocha undertones. |
| Compound having the structure: | A fruity aroma. |
| Perfume composition prepared according to Example I. | A pine aroma with excellent green, anisic, floral nuances and costus-like undertones. |
| Perfume composition prepared according to Example II. | An herbal fragrance having floral and anisic aroma nuances with a fruity, spicy character and chamomile and basil undertones. |
| Perfume composition prepared according to Example III. | A rosemary fragrance with spicy and fruity aroma nuances and a coffee/mocha undertone. |

EXAMPLE VII

PREPARATION OF A DETERGENT COMPOSITION

A detergent is prepared from the following ingredients according to Example I of Canadian Pat. No. 1,007,948:

| | Percent by Weight |
|---|---|
| "Neodol 56-11" (a C$_{14}$–C$_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. 100 gram samples of this detergent are individually admixed with 0.15 gram samples of the perfumery substances set forth in Table V below. Each of the resulting mixtures have excellent aromas as stated in Table V below:

TABLE V

| Substance | Fragrance Character |
|---|---|
| Compound having the structure: | A green, anisic and floral aroma with costus-like undertones. |
| Compound having the structure: | A floral, anisic, fruity, chamomile/basil-like aroma profile. |
| Compound having the structure: | A spicy, fruity aroma with coffee-mocha undertones. |

TABLE V-continued

| Substance | Fragrance Character |
|---|---|
| Compound having the structure:<br> | A fruity aroma. |
| Perfume composition prepared according to Example I. | A pine aroma with excellent green, anisic, floral nuances and costus-like undertones. |
| Perfume composition prepared according to Example II. | An herbal fragrance having floral and anisic aroma nuances with a fruity, spicy character and chamomile and basil undertones. |
| Perfume composition prepared according to Example III. | A rosemary fragrance with spicy and fruity aroma nuances and a coffee/mocha undertone. |

EXAMPLE VIII

PERFUMED LIQUID DETERGENT

Concentrated liquid detergents with aroma nuances as set forth in Table VI below are prepared containing 0.10%, 0.15% and 0.20% of the substances as set forth in Table VI below. They are prepared by adding and homogeneously admixing the appropriate quantities of the perfumery substances as set forth in Table VI below in the liquid detergents. The detergents all possess aromas as set forth in Table VI below, the intensities increasing with greater concentrations of perfumery substances.

TABLE VI

| Substance | Fragrance Character |
|---|---|
| Compound having the structure:<br>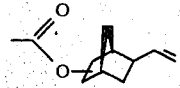 | A green, anisic and floral aroma with costus-like undertones. |
| Compound having the structure:<br>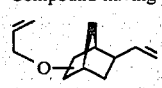 | A floral, anisic, fruity, chamomile/basil-like aroma profile. |
| Compound having the structure:<br>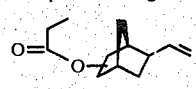 | A spicy, fruity aroma with coffee-mocha undertones. |
| Compound having the structure:<br> | A fruity aroma. |
| Perfume composition prepared according to Example I. | A pine aroma with excellent green, anisic, floral nuances and costus-like undertones. |
| Perfume composition prepared according to Example II. | An herbal fragrance having floral and anisic aroma nuances with a fruity, spicy character and chamomile and basil undertones. |
| Perfume composition prepared according to Example III. | A rosemary fragrance with spicy and fruity aroma nuances and a coffee/mocha undertone. |

EXAMPLE IX

COLOGNE AND HANDKERCHIEF PERFUME SUBSTANCES

Perfumery substances as set forth in Table VII below are incorporated into colognes at concentrations of 2.0%, 2.5%, 3.0%, 3.5% and 4.0% in 75%, 80%, 85%, 90% and 95% aqueous ethanol solutions; and into handkerchief perfumes at concentrations of 15%, 20%, 25%, 30% and 35% (in 75%, 80%, 85%, 90% and 95% aqueous ethanol solutions). Distinct and definitive fragrances as set forth in Table VII below are imparted to the colognes and to the handkerchief perfumes:

TABLE VII

| Substance | Fragrance Character |
|---|---|
| Compound having the structure:<br>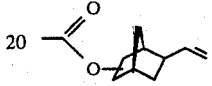 | A green, anisic and floral aroma with costus-like undertones. |
| Compound having the structure:<br>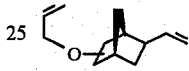 | A floral, anisic, fruity, chamomile/basil-like aroma profile. |
| Compound having the structure:<br>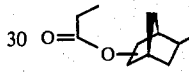 | A spicy, fruity aroma with coffee-mocha undertones. |
| Compound having the structure:<br>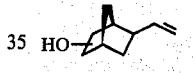 | A fruity aroma. |
| Perfume composition prepared according to Example I. | A pine aroma with excellent green, anisic, floral nuances and costus-like undertones. |
| Perfume composition prepared according to Example II. | An herbal fragrance having floral and anisic aroma nuances with a fruity, spicy character and chamomile and basil undertones. |
| Perfume composition prepared according to Example III. | A rosemary fragrance with spicy and fruity aroma nuances and a coffee/mocha undertone. |

EXAMPLE X

TOOTHPASTE FLAVOR FORMULATION

The following basic toothpaste flavor formulation is prepared:

| Ingredients | Parts by Weight |
|---|---|
| Cardamom oil | 0.2 |
| Clove oil | 1.0 |
| Spearmint oil | 2.0 |
| Peppermint oil | 96.8 |

This flavor formulation is divided into four portions. Eight parts by weight of the first portion is combined with two parts by weight of anethol. Eight parts by weight of each of the second, third and fourth portions of this flavor are combined, respectively, with:

a. Two parts by weight of a 50:50 mixture of 5- and 6-vinyl-2-norbornanol acetate b. Two parts by weight of a 50:50 mixture of 5- and 6-vinyl-2-allyloxy norbornane c. Two parts by weight of a mixture (50:50) of 5- and 6-vinyl-2-norbornane methanol propionate All of the flavors are compared in water at the rate of 10 ppm and evaluated by the bench panel. All four flavors have a sweet, anise-like character but the flavors containing the norbornyl ethers and esters have, in addition, a fuller licorice related note and also have pleasant, sweet, fruity flavors. Therefore, the flavors containing the norbornyl ethers and esters are considered by the bench panel as being better and more suitable toothpaste flavors with unique flavor effects.

EXAMPLE XI

The substantially pure 5-vinyl-2-norbornanol acetate is added to root beer (Barrelhead, produced by Canada Dry Corporation of Maspeth, N.Y., a division of the Norton Simon Corporation) at the rate of 0.5 ppm and submitted to a bench panel. The 5-vinyl-2-norbornanol acetate improves the woody, rooty notes insofar as the aroma and taste of the root beer are concerned. Therefore, the beverage containing the 5-vinyl-2-norbornanol acetate is preferred by a bench panel over the beverage which does not contain said 5-vinyl-2-norbornanol acetate. The same results are imparted when instead of 5-vinyl-2-norbornanol acetate, 6-vinyl-2-norbornanol acetate is added. Also, the same effects are imparted when a 50:50 mixture if 5-vinyl-2-norbornanol acetate and 6-vinyl-2-norbornanol acetate are added.

EXAMPLE XII

BASIC FLAVOR FORMULATION

| Ingredients | Parts by Weight |
| --- | --- |
| Cardamom oil | 0.2 |
| Clove oil | 1.0 |
| Spearmint oil | 2.0 |
| Peppermint oil | 85.4 |
| 5-vinyl-2-norbornanol acetate | 12.0 |
| 5-vinyl-2-allyoxy norbornane | 3.0 |
| 6-vinyl-2-norbornane methanol propionate | 7.2 |

EXAMPLE XIII

A. POWDER FLAVOR COMPOSITION 20 grams of the flavor composition of Example XII is emulsified in a solution containing 300 grams gum acacia and 700 grams water. The emulsion is spray-dried with a Bowen Lab Model Drier utilizing 260 c.f.m. of air with an inlet temperature of 500° F., an outlet temperature of 200° F. and a wheel speed of 50,000 rpm.

B. SUSTAINED RELEASE FLAVOR

The following mixture is prepared:

| Ingredients | Parts by Weight |
| --- | --- |
| Flavor composition of Example XII | 20 |
| Propylene glycol | 9 |
| Cab-O-Sil ® M-5 (brand of silica produced by the Cabot Corporation of 125 High Street, Boston, Mass. 02110: Physical properties: Surface area: 200 m²/gm Nominal particle size: 0.012 microns | |

| Ingredients | Parts by Weight |
| --- | --- |
| Density: 2.3 lbs/cu.ft.) | 5.00 |

The Cab-O-Sil ® is dispersed in the liquid anise flavor composition of Example XII with vigorous stirring thereby resulting in a viscous liquid. 71 parts by weight of the powder flavor composition of Part A supra, is then blended into the said viscous liquid, with stirring, at 25° C. for a period of 30 minutes resulting in a dry, free-flowing sustained release flavor powder.

EXAMPLE XIV 10 parts by weight of 50 Bloom pigskin gelatin is added to 90 parts by weight of water at a temperature of 150° F. The mixture is agitated until the gelatin is completely dissolved and the solution is cooled to 120° F. 20 parts by weight of the liquid flavor composition of Example XII is added to the solution which is then homogenized to form an emulsion having particle size typically in the range of 2–5 microns. This material is kept at 120° F. under which conditions the gelatin will not jell.

Coacervation is induced by adding, slowly and uniformly 40 parts by weight of a 20% aqueous solution of sodium sulphate. During coacervation, the gelatin molecules are deposited uniformly about each oil droplet as a nucleus.

Gelation is effected by pouring the heated coacervate mixture into 1,000 parts by weight of 7% aqueous solution of sodium sulphate at 65° F. The resulting jelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XV

CHEWING GUM 100 parts by weight of chicle are mixed with 4 parts by weight of the flavor prepared in accordance with Example XII. 300 parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long-lasting sweet, anise flavor.

EXAMPLE XVI

CHEWING GUM 100 parts by weight of chicle are mixed with 18 parts by weight of the flavor prepared in accordance with Example XII. 300 parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long-lasting sweet anise flavor.

EXAMPLE XVII

TOOTHPASTE FORMULATION

The following separate groups of ingredients are prepared:

| Parts by Weight | Ingredient |
|---|---|
| Group "A" | |
| 30.200 | Glycerine |
| 15.325 | Distilled water |
| .100 | Sodium benzoate |
| .125 | Saccharin sodium |
| .400 | Stannous fluoride |
| Group "B" | |
| 12.500 | Calcium carbonate |
| 37.200 | Dicalsium phosphate (dihydrate) |
| Group "C" | |
| 2.000 | Sodium n-lauroyl sarcosinate (foaming agent) |
| Group "D" | |
| 1.200 | Flavor material of Example XII |
| 100.00 (total) | |

Procedure:
1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing, until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure, yields a pleasant sweet, anise flavor, of constant strong intensity throughout said procedure (1–1.5 minutes).

EXAMPLE XVIII

CHEWABLE VITAMIN TABLETS

The flavor material produced according to Example XII is added to a chewable vitamin tablet formulation at a rate of 10 gm/Kg which chewable vitamin tablet formulation is prepared as follows:

In a Hobart Mixer, the following materials are blended to homogeneity:

| | Gms/1000 tablets |
|---|---|
| Vitamin C (ascorbic acid) as ascorbic acid-sodium ascorbate mixture 1:1 | 70.00 |
| Vitamin B$_1$ (thiamine mononitrate) as Rocoat® thiamine mononitrate 33⅓% (Hoffman La Roche) | 4.0 |
| Vitamin B$_2$ (riboflavin) as Rocoat® riboflavin 33⅓% | 5.0 |
| Vitamin B$_6$ (pyridoxine hydrochloride) as Rocoat® pyridoxine hydrochloride 33⅓% | 4.0 |
| Niacinamide as Rocoat® niacinamide 33⅓% | 33.0 |
| Calcium pantothenate | 11.5 |
| Vitamin B$_{12}$ (cyanocobalamin) as Merck 0.1% in gelatin | 3.5 |
| Vitamin E (dl-alpha tocopheryl acetate) as dry Vitamin E acetate 33⅓% Roche | 6.6 |
| d-biotin | 0.044 |
| Flavor of Example XII | (as indicated above) |
| Certified lake color | 5.0 |
| Sweetener-sodium saccharin | 1.0 |
| Magnesium stearate lubricant | 10.0 |
| Mannitol q.s. to make | 500.0 |

Preliminary tablets are prepared by slugging with flatfaced punches and grinding the slugs to 14 mesh. 13.5 G dry Vitamin A acetate and 0.6 g. Vitamin D are then added as beadlets. The entire blend is then compressed using concave punches at 0.5 g each.

Chewing of the resultant tablets yields a pleasant, longlasting, consistently strong sweet anise flavor for a period of 12 minutes.

EXAMPLE XIX

CHEWING TOBACCO

Onto 100 pounds of tobacco for chewing (85% Wisconsin leaf and 15% Pennsylvania leaf) the following casing is sprayed at a rate of 30%.

| Ingredients | Parts by Weight |
|---|---|
| Corn syrup | 60 |
| Licorice | 10 |
| Glycerine | 20 |
| Fig juice | 4.6 |
| Prune juice | 5 |
| Flavor material of Example XII | 0.4 |

The resultant product is redried to a moisture content of 20%. On chewing, this tobacco has an excellent substantially consistent, long-lasting licorice nuance in conjunction with the tobacco note.

Throughout the instant specification, it is intended that the structure:

wherein R represents acetyl, propionyl or allyl define structures in various isomeric configurations, for example, the configurations having the structures:

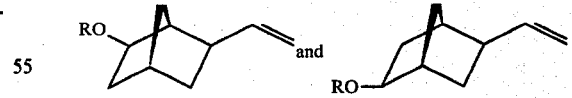

as well as configurations which are "endo" and "exo", to wit:

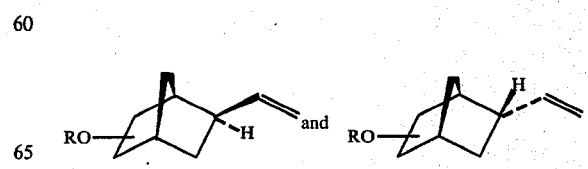

as well as more specific configurations such as those defined according to the structures:

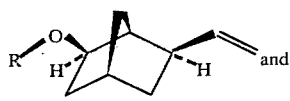

and

What is claimed is:

1. A process for augmenting or enhancing the aroma of a solid or liquid anionic, cationic, nonionic or zwitterionic detergent comprising the step of adding to a solid or liquid anionic, cationic, nonionic or zwitterionic detergent base, an aroma augmenting or enhancing quantity of a mixture of compounds represented by the structure:

wherein in one of the molecules of the mixture the "OR" moiety exists at the "5" position on the norbornyl ring structure and in the other of the molecules of the mixture the "OR" moiety exists at the "6" position on the norbornyl ring structure; and wherein R represents a moiety selected from the group consisting of acetyl and propionyl and wherein in the mixture the R moieties are identical.

* * * * *